United States Patent [19]

Wadsworth

[11] Patent Number: 4,686,978

[45] Date of Patent: Aug. 18, 1987

[54] INSTRUMENTATION FOR IMPLANTATION OF AN ELBOW PROSTHESIS

[76] Inventor: Thomas G. Wadsworth, 22 Hyde Park Square, London, W.2, England

[21] Appl. No.: 294,889

[22] Filed: Aug. 21, 1981

Related U.S. Application Data

[60] Continuation of Ser. No. 139,700, Apr. 14, 1980, abandoned, which is a division of Ser. No. 931,319, Aug. 7, 1978, abandoned.

[51] Int. Cl.$^4$ .............................................. A61B 17/00
[52] U.S. Cl. .................................................. 128/303 R
[58] Field of Search ............ 128/303 R, 92 EC, 92 E, 128/305; 3/1.9–1.913; 145/24, 25

[56] References Cited

U.S. PATENT DOCUMENTS

| 113,075 | 3/1871 | McConnell | 142/25 |
| D. 249,705 | 9/1978 | London | 128/92 E X |

FOREIGN PATENT DOCUMENTS 8154 of 1901 United Kingdom .................. 145/25

OTHER PUBLICATIONS

Zimmer Product Encyclopedia, cover page and pp. A34, A80, A81 and B148 (Jun. 1978).

*Primary Examiner*—Michael H. Thaler
*Attorney, Agent, or Firm*—Carroll F. Palmer

[57] ABSTRACT

Prosthetic replacement of an elbow joint is accomplished using a humeral component having an articular surface comprising a concave surface in the coronal plane and a convex surface in the sagittal plane with such component being cemented along a superior U-slot to a surgically prepared humeral bone. The prosthesis also comprises an ulnar component having an articular surface defined by a convex surface in the coronal plane and a concave surface in the sagittal plane, its undersurface having a longitudinal keel and a dependent stem by which it is cemented to the surgically prepared ulnar bone. Optionally, the prosthesis may include a radial head component in the form of a dished button that can be cemented to the surgically prepared radial bone by a depending stem.

2 Claims, 17 Drawing Figures

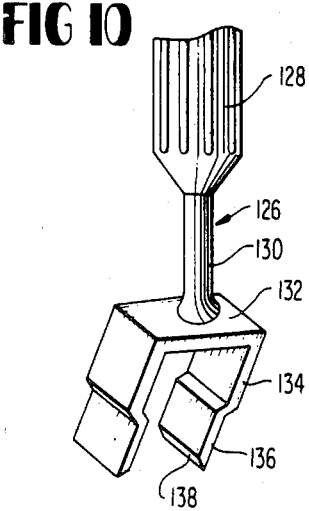
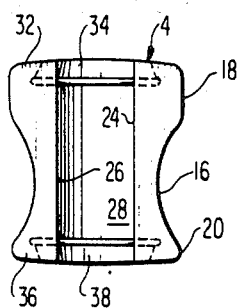
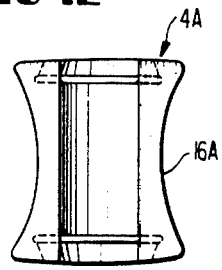
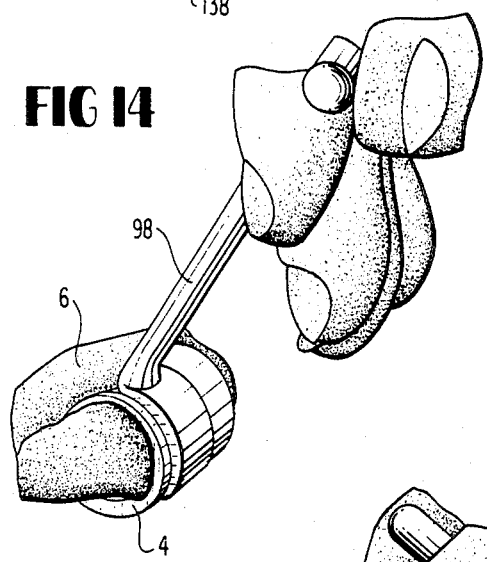
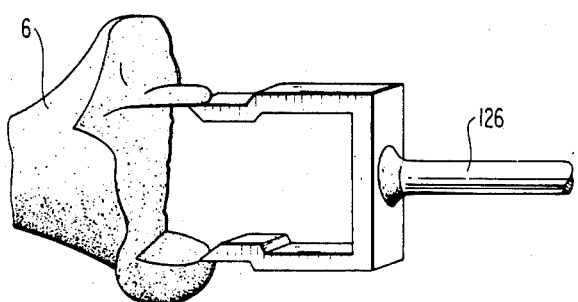
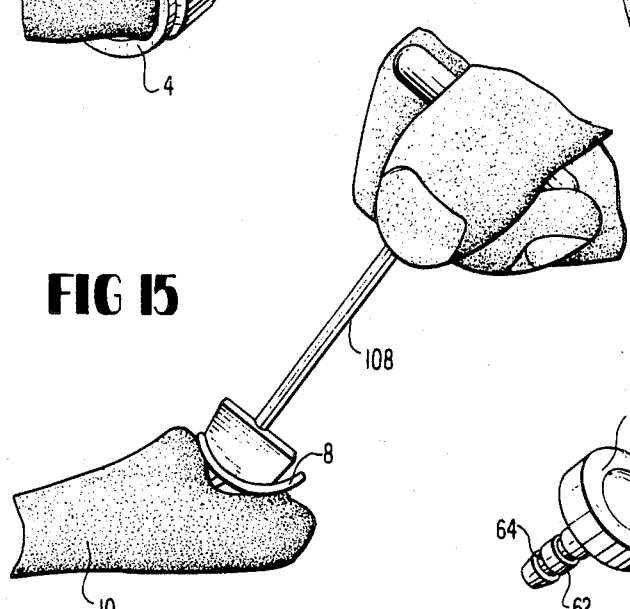
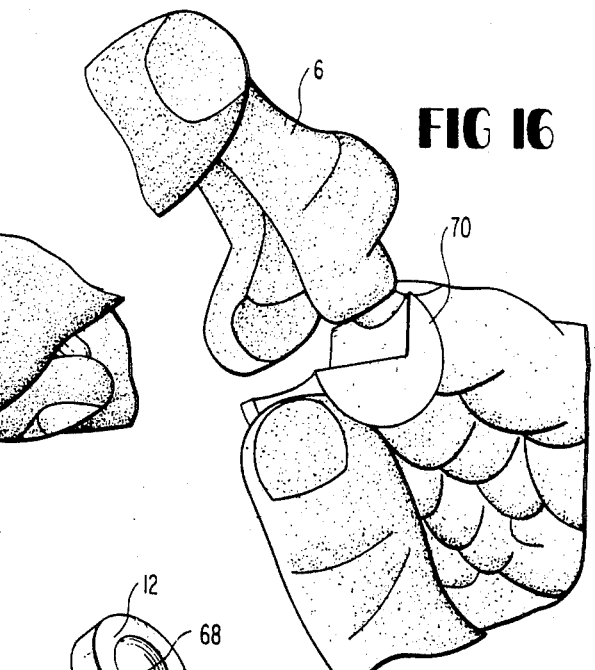
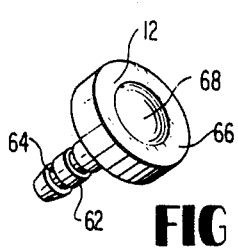

INSTRUMENTATION FOR IMPLANTATION OF AN ELBOW PROSTHESIS

This is a continuation of application Ser. No. 139,700 filed Apr. 14, 1980, abandoned, which is a division of application Ser. No. 931,319 filed Aug. 7, 1978, abandoned.

BACKGROUND OF THE INVENTION

1. Field of the Invention

This invention relates to a prosthesis for replacement of arthritic or damaged elbow joints. More particularly, it concerns a form of elbow joint prosthesis that has good joint stability with minimum bone removal while providing normal flexion and extension motion; there is no in-built constraint and so little strain on the seating of the prosthesis.

2. Description of the Prior Art

In general, prosthetic replacement of the elbow has proved a difficult and often disappointing task over the years and this has been the experience of most surgeons in this field. In the past, it was common to replace the elbow joint by means of a constrained prosthesis, usually consisting of a large stem inserted into the humerus and another into the ulna and the two parts of the component linked together by an axle pin. The strong forces on the elbow tend to disrupt the prosthesis from the bone and a very great deal of bone had to be removed to put in such a prosthesis, resulting in the long-term in a disastrous situation very often if the prosthesis has, in fact, to be removed.

There has been a move in recent times to a surface replacement of the elbow joint and my work in this area led to the development of a constrained device with a T-slot stability factor which is described in U.S. Pat. No. 4,079,469. Numerous other U.S. patents have issued describing bone joint prosthesis of which the following is a representative listing: Nos.

2,784,416
3,547,115
3,748,662
3,798,679
3,801,990
3,816,854
3,840,905
3,852,831
3,869,729
3,886,599
3,919,725
3,990,116

In spite of the numerous procedures and devices previously developed and used for elbow reconstruction, there exists a need for further improvement particularly as regards resulting joint stability, minimal removal of bone for insertion and allowance for normal flexion and extension motion as well as minimal strain on the seating of the prosthesis.

OBJECTS

A principal object of the present invention is the provision of new forms of bone joint prosthesis.

Another object is the provision of a type of elbow prosthesis that is characterized by:

(i) Minimal removal of bone for insertion.
(ii) Protection of the ulnar nerve within the cubital tunnel by preservation of the medial lip of the trochlea.
(iii) Allowance for normal flexion and extension motion at the elbow.
(iv) Stability, which is importantly achieved by the arrangement of the joint articulation that guards against undue medial and lateral movement which would be abnormal for the elbow.
(v) Additional overall stability that ensues from minimal interference with ligaments and capsule associated with the operative technique.
(vi) Lightness in weight.
(vii) Relatively inexpensive to produce.
(viii) Should removal of the implant be necessary, e.g., for infection, the patient would be left with a conventional excision arthroplasty which should give useful function.

A further object is the provision of an elbow prosthesis useful in rehabilitating a patient with a severe arthritic problem of the elbow and which may be easily inserted by any orthopedic surgeon.

Other objects and further scope of applicability of the present invention will become apparent from the detailed description given hereinafter; it should be understood, however, that the detailed description, while indicating preferred embodiments of the invention, is given by way of illustration only, since various changes and modifications within the spirit and scope of the invention will become apparent to those skilled in the art from this detailed description.

SUMMARY OF THE INVENTION

These objects are accomplished according to the present invention by the provision of an elbow prosthesis that comprises a small humeral component, preferably made of plastic, and a small, independent ulnar component made of metal. If necessary, for special cases, the prosthesis may also include a small radial component. None of the components in the reconstructed elbow joint are mechanically attached to the other, i.e., they contact one another along specially formed articular surfaces. In the humeral component, the articular surface is concave in the coronal plane ending laterally in a convex surface and in the sagittal plane the surface is convex at the level of the concave surface. The humeral component has a superior U-slot by which it is cemented to the surgically prepared humeral bone.

In the ulnar component, the articular surface is convex in the coronal plane and concave in the sagittal plane. Its undersurface has a longitudinal keel from which depends a stem by which the component is cemented onto and into the surgically prepared ulnar bone.

The objects are also accomplished by the provision of instrumentation comprising two chisels for use in surgically preparing the humeral bone and two impactors for positioning and accurately holding the humeral and ulnar components while they are cemented to the humerus and ulna.

Trial humeral components are also provided for use in assessing the depth of humeral bone to be removed and also for sizing of the humeral component to fit particular patients.

BRIEF DESCRIPTION OF THE DRAWINGS

A more complete understanding of the new elbow replacement prosthesis of the invention may be had by reference to the accompanying drawings in which:

FIG. 10 is a perspective view of another chisel used in implanting the humeral component.

FIG. 11 is a plan view of the usual form of humeral component of the new prosthesis.

FIG. 12 is a plan view of the special form of humeral component used for replacement of a totally destroyed elbow joint.

FIG. 13 is a fragmentary perspective view of a chisel cutting the humerus for implantation of the humeral component.

FIG. 14 is a fragmentary perspective view of a humeral impactor pushing the humeral component onto the humeral bone during cementing.

FIG. 15 is a fragmentary perspective view of an ulnar impactor pushing the ulnar component onto the ulnar bone during cementing.

FIG. 16 is a fragmentary perspective view of a trial humeral component being applied to the humerus.

FIG. 17 is a perspective view of a radial head component that may be used on occasion in the new elbow replacement prosthesis.

DESCRIPTION OF PREFERRED EMBODIMENTS

Figure 1:
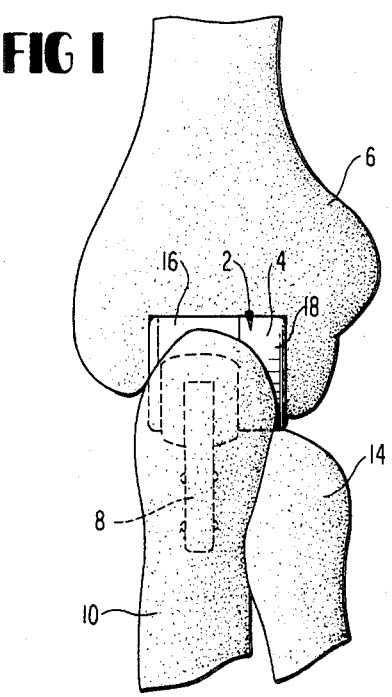
FIG. 1 is a fragmentary anterior elevation of an elbow prosthesis of the invention illustrated as implanted in the humerus and ulna.
Figure 2:
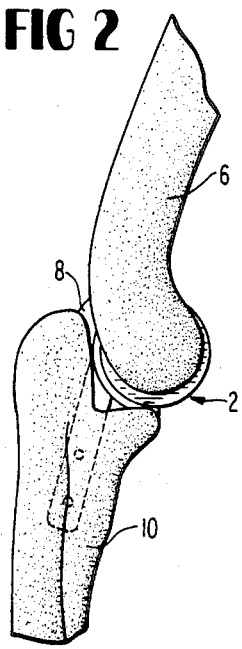
FIG. 2 is a fragmentary lateral elevation of the elbow prosthesis with humerus and ulna in extension position (0°).
Figure 3:
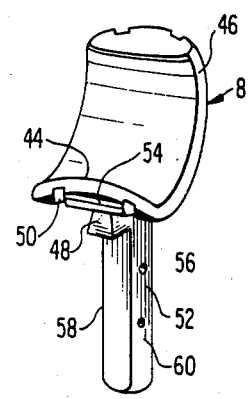
FIG. 3 is a perspective view of an ulnar component of the prosthesis.
Figure 4:
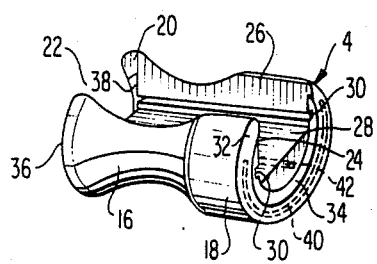
FIG. 4 is a perspective view of a humeral component of the prosthesis.

Referring in detail to the drawings, the elbow replacement prosthesis 2 basically comprises a humeral component 4 that is implanted in the humerus 6 and an ulnar component 8 implanted in the ulna 10. Optionally, it may comprise a radial component 12 (FIG. 17) that is implanted in the radius 14.

The humeral component 4 has a concave surface 16 in the coronal plane that is joined laterally to a convex surface 18, the latter partially replacing the capitulum bone of the humerus upon implantation. In the sagittal plane, the surface 20 is convex at the level of the concave surface in the coronal plane for articulation with the ulnar component 8. The surfaces 16, 18 & 20 form the articular surface of the humeral component 4.

A slightly different form of humeral component 4A is used in the prosthesis for replacement of a totally destroyed elbow joint (see FIG. 12). The component 4A is the same in all particulars to component 4 except that the concave articular surface 16A in the coronal plane extends right across the whole length of the component 4A and there is no convex surface such as surface 18 in component 4.

The surface for attaching the humeral component 4 to the humerus comprises a superior U-slot 22 with chordal anterior wall 24, posterior wall 26 and flat floor 28. Longitudinal grooves 30 are formed in the walls 24 and 26 for keying of cement for implantation of the component 4. The lateral wall 32 has a peripherial groove 34 and the medial wall 36 a similar groove 38 for keying of cement. Annular wire markers 40 are imbedded in the walls 32 and 26 and a longitudinal wire marker 42 is embedded in the floor 28 so that position of the prosthesis can be determined by x-ray inspection, after implantation, of both the coronal and sagittal planes by means of the three markers.

The main articulating surface of component 4 describes a gentle concave curve in the coronal plane which allows for simple and effective engagement with the convex surface 44 in the coronal plane of the ulnar component 8 Thus, a limited amount of sideway rotation motion is allowed which may at times become necessary in order to avoid undue strain on the bony attachments to the prosthetic components.

In the sagittal plane of the component 4, the convex articulating surface 16 increases in radius from its center in both the medial and lateral directions to a similar extent where the convex surfaces 18 and 20 take over.

The articular surface of ulnar component 8 comprises the convex surface 44 in the coronal plane and a concave surface 46 in the sagittal plane. These surfaces allow for accurate and easy articulation with surface 16 of the humeral component 4.

The bone attaching portion of the ulnar component 8 comprises a longitudinal keel 48 with grooves 50 running longitudinally along beside the keel 48 for keying of cement in implantation. A stem 52 depends from the keel 48 and undersurface 54 of the articulating area for insertion into the ulna. The stem 52 has nipples 56 on both the medial surface 58 and lateral surface 60 for keying into cement for implantation.

The ulnar component 8 fits onto and into a surgically prepared ulna. The angle at which the stem 52 describes with the articulating area is selected to control anteversion seating of the component 8 in the ulnar bone 10. This is important for antero-posterior stability of the reconstructed elbow joint. A reconstructed elbow joint according to the invention may also include a radial component 12 (FIG. 17) In actual fact, although the head of the radius 14 is always removed for insertion of the prosthesis, it is not always necessary to replace this removed bone. However, in necessary cases, the bone may be replaced with the radial component 12 which comprises a distal key portion 62 having cement keying grooves 64 and an integral proximal bearing button 66 with dished surface 68. If the component 12 is used, it is implanted into the surgically prepared radius 14 and fixed in place with cement in a manner similar to implant of the ulnar component 8.

In order to assess the depth of humeral bone to be removed and also for sizing of a component to fit a particular patient, trial humeral components may be used, i.e., special component 70 or usual humeral component 72. The component 70 corresponds to the permanent special component 4A and component 72 to the permanent usual component 4.

The component 70 comprises the concave surface 74 in the coronal plane, lateral wall 76 and medial wall 78. Instead of a U-shaped slot as in the permanent component 4A, component 70 has an L-shaped slot defined by the posterior wall 80 and the floor 82.

The component 72 comprises the concave surface 84 in the coronal plane, convex surfaces 86 & 88, medial wall 90, lateral wall 92 and an L-shaped slot defined by posterior wall 94 and floor 96.

The components 70 & 72, unlike their permanent counterparts 4 and 4A do not include wire markers or keying grooves, but, aside from this and the L-shaped slots, components 70 & 72 are the same as 4A & 4.

In reconstruction of an elbow joint, only one style of components 4, 4A or 70 need be used. However, with component 72, right and left hand styles must be used dependent upon whether a right or left elbow is being reconstructed.

A variety of materials are available from which to construct components 4, 8 and 12. Advantageously, the humeral component is formed of inert plastic, e.g., high density polyethylene, and the ulnar component 8 and radial component 12 are made of corrosion-resistant metal, e.g., the chromium alloy "Alivium". The impactors and chisels are advantageously formed of stainless steel or equivalent metal except for the end of the ulnar impactor in contact with the ulnar prosthesis.

The design of the components 4 and 8 as described enables them to be made and used in an average size adaptable to a large number of patients. However, it should be recognized that different sizes may be necessary and this can be determined by use of sized trial components 70 or 72.

Figure 5:
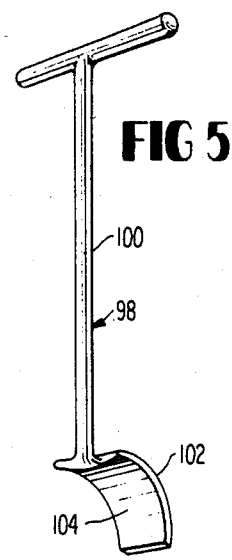
FIG. 5 is a perspective view of a humeral component impactor.
Figure 6:
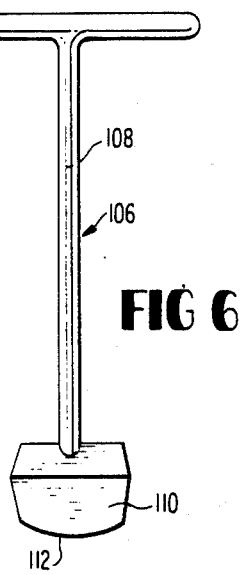
FIG. 6 is a perspective view of an ulnar component impactor.
Figure 7:
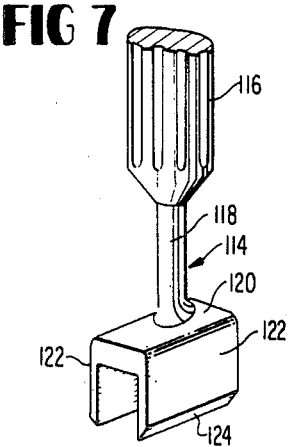
FIG. 7 is a perspective view of a chisel used to cut the humerus for implanting the humeral component.
Figure 8:
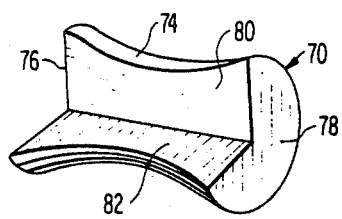
FIG. 8 is a perspective view of one embodiment of a trial humeral component used primarily for replacement of a totally destroyed elbow joint.
Figure 9:
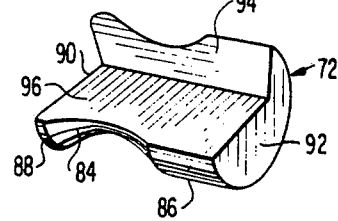
FIG. 9 is a perspective view of another embodiment of a trial humeral component.

Instrumentation for reconstruction of an elbow joint in accordance with the invention is shown in FIGS. 5-7 and 10.

The humeral impactor 98 (or pusher) comprises a T-shaped handle 100 fixed in the coronal plane to the integral distal end member 102 having its pushing surface 104 formed complimentarily to the concave-convex surface 16 of component 4. This enables impactor 98 to be put in position upon the humeral component easily and be held there accurately while cement hardens during implantation.

The ulnar impactor 106 also has a T-shaped handle 108, but this is fixed in the sagittal plane to the integral distal end member 110. The pushing surface 112 is formed complimentarily to the articulating surface 44 of component 8 to again provide easy placement and accurate holding during cementing.

Chisel 114 comprises mallet head 116, stem 118, base member 120 and two wings 122, each with chisel tips 124. The stem 118 is perpendicular to the base member 120, but offset from the center thereof for ease of access to the elbow joint. Chisel 114 is used to mark out the antero-posterior breath of the humeral bone to be removed in order to fit into the slot 22 of component 4. It also marks the depth: equivalent to that of the depth of the slot 22 in component 4.

Chisel 126 comprises mallet head 128, stem 130, base member 132, wings 134 with inset ends 136 and chisel tips 138. The wings 134 are in a different plane from the wings 122 of chisel 114.

Chisel 126 is used for accurately marking out the length of humeral bone to be removed and also to mark the depth since the inset ends 136 of the chisel are sized in length to compare with the depth of the body of component 4. Use of chisel 126 to mark out and cut away humeral bone from the humerus 6 is shown in FIG. 13. Chisel 114 is then used in the opposite plane to mark out the antero-posterior breath of bone removal. Upon completion of humeral bone removal in such manner, the humeral component 4, with cement applied to the surfaces of slot 22 is applied to the humerus 6 and held in place with impactor 98 as shown in FIG. 14 until the cement has set. The keel of the prepared humeral bone sits in the U-slot of component 4 and its medial and lateral ends sit against the medial and lateral walls of the prepared lower humerus.

The ulna is prepared to receive the stem 52 of ulna component 8. Cement is then applied to the stem 52 and undersurface 54 and the component 8 is inserted into and onto the upper end of the ulna 10. The component 8 is held in position as shown in FIG. 15 with impactor 108 until the cement is fully set. In the reconstructed joint, the ulnar component sits on the olecranon process of the ulnar bone and the stem 52 seats within that bone to give good stability to the component 8.

A preferred cement for use in the new joint reconstructions is self-hardening methyl methacrylate cement, but other body compatible cements may be used.

As previously indicated, trial humeral components may be used in order to assess the depth of humeral bone to be removed and also for sizing of a component to fit a particular patient. FIG. 16 illustrates the application of the trial component 70 to the surgically prepared humeral bone 6.

It is to be understood that FIGS. 13-16 are illustrative only and do not attempt to depict the actual appearance of the operations. Obviously, the actual surgical procedures would be conducted under sterile conditions with the surgeon's hands gloved and there would be flesh around the humerus and ulna.

In an elbow joint reconstructed in accordance with the invention, the articulating surfaces, e.g., 16 and 44, fit easily together and give a range of flexible movement between full extension (0°) to flexion position (150°). Stability is provided, in particular, by the intact medial ligament of the elbow and also by the lateral ligament, the anterior and posterior joint capsule and the adjacent musculature. Hence, any tendency for dislocation of the prosthesis is resisted by the natural anatomy and any lateral shift of the ulna is discouraged by the lateral convex part 18 of the humeral component 4. This is useful if trauma or undue strain is delivered to the elbow joint. Further, the prosthetic articulating arrangement allows for rotation of the ulna at the elbow, thus avoiding strain on the seating of the two components in strain situations.

Minimal bone is removed in the operative procedure which is a distinct advantage if there should be failure of the prosthesis for any reason, in which event, other surgical procedures can be easily accomplished.

The three humeral wire markers allow for accurate visualisation of the prosthesis by x-ray which is important in assessing wear and/or displacement after accidental trauma or loosening of the humeral component for any reason.

The embodiments of the invention in which an exclusive property or privilege is claimed are defined as follows:

1. Instrumentation for implantation of an elbow prosthesis comprising a humeral component having an articular surface that is curved concave in a coronal plane and curved convex in a sagittal plane and an ulnar component having an articular surface that is curved convex in the coronal plane and curved concave in the sagittal plane and is complementary to said articular surface of said humeral component, said instrumentation comprising a humeral impactor including an impactor head comprised of a thin curved end member of which a pushing surface is formed complementarily to said articular surface of said humeral component, and a stem extending from one end of said end member in a direction substantially perpendicularly away from said pushing surface, whereby said end member extends unilaterally from said stem.

2. Instrumentation for implantation of an elbow prosthesis comprising a humeral component having an articular surface that is curved concave in a coronal plane and curved convex is a sagittal plane and an ulnar component having an articular surface that is curved convex in the coronal plane and curved concave in the sagittal plane and complementary to said articular surface of said humeral component, said instrumentation comprising
 a chisel (114, 126) including a transverse base web (120,132),
 two substantially parallel blades (122–124, 134–136) extending from one side of said base web bounding therebetween a channel open at both ends thereof,
 said blades including respective substantially parallel knife edges (124,138) extending along the channel and the side walls of said channel being substantially parallel with each other and extending to said knife edges,
 said blades extending from said base web in planes that are not parallel to the plane of said stem and having offset portions proximal of said knife edges to mark the depth that said chisel will cut into the humeral bone of the patient into which said prothesis is to be implanted,
 a mallet head (116,128) and
 a stem (118,130) connecting said head to said base web, said stem being substantially perpendicular to said base web.

* * * * *